(12) United States Patent
LeDez et al.

(10) Patent No.: US 6,263,874 B1
(45) Date of Patent: Jul. 24, 2001

(54) COMBINED ANESTHETIC AND SCAVENGER MASK

(76) Inventors: Kenneth Michael LeDez, RR #1, Site 27, Box 51, Paradise, Newfoundland (CA), A1L 1C1; James Wing Au, 270 Frecker Drive, St. John's, Newfoundland (CA), A1E 5S5

( * ) Notice: Subject to any disclaimer, the term of this patent is extended or adjusted under 35 U.S.C. 154(b) by 0 days.

(21) Appl. No.: 09/182,482

(22) Filed: Oct. 30, 1998

Related U.S. Application Data

(60) Provisional application No. 60/065,592, filed on Nov. 18, 1997, now abandoned.

(51) Int. Cl.[7] .................................................. A62B 18/02
(52) U.S. Cl. ................ 128/206.21; 128/910; 128/205.25
(58) Field of Search ......................... 128/202.16, 205.19, 128/205.12, 910, 206.21, 863, 205.25

(56) References Cited

U.S. PATENT DOCUMENTS

| | | |
|---|---|---|
| 3,867,936 | 2/1975 | Kelley . |
| 4,109,651 | 8/1978 | Steigerwald . |
| 4,112,940 | 9/1978 | Parkes . |
| 4,219,020 * | 8/1980 | Czajka ............................ 128/205.25 |
| 4,248,218 | 2/1981 | Fischer . |
| 4,265,239 | 5/1981 | Fischer, Jr. et al. . |
| 4,312,339 | 1/1982 | Thompson, Sr. . |
| 4,527,558 | 7/1985 | Hoenig . |
| 4,770,169 * | 9/1988 | Schmoegner et al. ............... 128/910 |
| 4,807,617 | 2/1989 | Nesti . |
| 4,848,366 | 7/1989 | Aita et al. . |
| 4,895,172 * | 1/1990 | Lindkvist ............................ 128/910 |
| 4,905,685 | 3/1990 | Olsson . |
| 5,044,361 | 9/1991 | Werner et al. . |
| 5,044,363 | 9/1991 | Burkhart . |
| 5,109,839 * | 5/1992 | Blasdell et al. .................. 128/203.12 |
| 5,127,411 * | 7/1992 | Schoolman et al. .................. 128/863 |
| 5,265,595 * | 11/1993 | Rudolph ........................... 128/204.18 |
| 5,370,110 | 12/1994 | Corn . |
| 5,419,317 * | 5/1995 | Blasdell et al. ...................... 128/910 |
| 5,471,979 | 12/1995 | Psaros et al. . |
| 5,524,616 | 6/1996 | Smith et al. . |
| 5,560,354 * | 10/1996 | Berthon-Jones et al. ....... 128/205.25 |
| 5,596,983 * | 1/1997 | Zander et al. .................. 128/204.18 |
| 5,636,627 * | 6/1997 | Rochester ............................ 128/910 |
| 5,657,752 | 8/1997 | Landis et al. . |
| 5,660,171 * | 8/1997 | Kimm et al. .................... 128/204.23 |
| 5,662,101 * | 9/1997 | Ogden et al. ................... 128/205.25 |
| 5,676,133 * | 10/1997 | Hickle et al. ................... 128/205.25 |
| 5,715,813 | 2/1998 | Guevrekian, Jr. et al. . |
| 5,794,615 * | 8/1998 | Estes .............................. 128/204.23 |
| 5,970,975 * | 10/1999 | Estes et al. ..................... 128/204.23 |
| 6,006,748 * | 12/1999 | Hollis .............................. 128/205.24 |

* cited by examiner

Primary Examiner—Aaron J. Lewis
Assistant Examiner—Joseph F. Weiss, Jr.
(74) Attorney, Agent, or Firm—Nath & Associates PLLC; Gary M. Nath; Jerald L. Meyer

(57) ABSTRACT

A combined nasal anaesthesia breathing mask and oral scavenging hood is provided herein. Such combination includes a nasal anaesthesia breathing mask with inlet means to the nasal anaesthesia mask for connection to a conventional anaesthesia breathing circuit. An oral scavenging hood is operatively associated with or is physically associatable with respect to, the nasal anaesthesia breathing mask for placement over only the mouth of the patient undergoing inhaled sedation. An inlet means is provided to the oral scavenging hood for connection to a conventional scavenging circuit. The inventive concept is that there is no gaseous communication between the nasal anaesthesia breathing mask and the oral scavenging hood. In this way, inhalation of anaesthesia gas can take place simultaneously with the scavenging of exhaled gases.

11 Claims, 5 Drawing Sheets

COMBINED ANESTHETIC AND SCAVENGER MASK

This application is a continuation-in-part of provisional application Serial No. 60/065,592 filed Nov. 18, 1997, now abandoned.

BACKGROUND OF THE INVENTION

This invention relates to a oral scavenging hood for use when a nasal anesthesia mask is used for inhaled sedation.

The administration of anesthetic or analgesic (inhalation sedation) gas to patients involves a mask (hood) which is placed over the nose of the patient and the introduction of a controlled amount of gas, through the mask, to the patient. Heretofore, such gas that either has leaked from the mask perimeter or was exhaled by the patient has been allowed to dissipate into the ambient environment. Concerns about the danger presented by this escaping gas in the environment of an operating room, particularly the side effects on personnel who are subject to this environment on a continual basis, have prompted increased attention and approaches to the elimination of such gas escape. Consequently, nasal anesthesia masks including scavenging means are well-known in the art. Among such art, are the following patents:

Kelley U.S. Pat. No. 3,867,936 Patented Feb. 25, 1975

That patent provided a structure whereby while anaesthetic gas which was administered to a patient, and which was exhaled from the patient was passed through a replaceable, man-transportable absorber unit to absorb the anaesthetic gas employed.

Parkes U.S. Pat. No. 4,112,940 Patented Sep. 12, 1978

That patent provided a scavenging valve for anaesthesia gas which was released in pediatric anaesthesia apparatus which was of generally conical configuration and which had an axial bore extending therethrough from an open base to an open apex. A control valve comprised a pair of nipples, each of generally-conical configuration, in base-to-base relation with an axial bore extending therethrough from one open apex end to the other. The control valve had a radially-extending bore which tapered down from the bases. The control valve coupled an anaesthesia bag to the scavenging valve and had a gas flow control and shut off plate pivotally mounted in the bore thereof in the area of the bases of the control valve. A manually-operable control member was provided outside the control valve.

Brown U.S. Pat. No. 4,015,598

That patent disclosed a double wall face mask, i.e., a mask over a mask. The inner mask defined a chamber over the patient's face communicating with a source of gas to be inhaled. The outer mask enclosed and defined an exhaust chamber outside of the inner mask, the exhaust chamber communicating with a gas removal line. A check valve opened the facial chamber to the exhaust chamber during exhalation and the exhaust chamber was open to the surrounding atmosphere adjacent the face-engaging perimeter of the inner mask to draw escaped gases from the surrounding atmosphere into the exhaust passage for disposal.

Czajka U.S. Pat. No. 4,219,020 Patented Aug. 26, 1980

That patent provided a mask assembly for administering a gas to be inhaled by an individual including a mask body to fit over the nose of the individual, and against the surrounding facial area of said individual, the mask body terminating in a peripheral surface contoured to fit against the facial area of said individual and when so positioned defining therewith a mask chamber, the mask body also including an inlet port which was adapted to be operatively connected to a source of gas to be administered to said individual thereby to direct said gas to said mask chamber. Valve means were provided including a valve body member disposed through the mask body in an area of the mask body remote from the contoured peripheral surface, the valve body member including an exhalation valve member movable between a first seated closed position during inhalation of the individual and a second open position during exhalation of said individual, the valve body member including a first exhaust chamber formed about the exhalation valve member to receive exhalation gas of said individual flowing through said exhalation valve member and a second annular exhaust chamber formed of a pair of substantially frusto-conically shaped members radiating outwardly from said valve body member and spaced from each other to define said second annular exhaust chamber. Means afforded fluid communication between the first and second exhaust chambers and an outlet port which was adapted to be connected to a vacuum source in one of the exhaust chambers, thereby to provide a source of vacuum to each of the first and second exhaust chambers to exhaust gas exhaled by said individual. The pair of radiating members defined an area at their termini, the area being disposed circumferentially and outwardly of the mask body and being located distantly from the periphery surface and the facial area of the individual when the mask was in use and being spaced from said inlet port. The pair of radiating members had inlet means to the annular exhaust chamber near the outer edge surface of the annular exhaust chamber, thereby to establish a suction effect about the whole exterior of the mask body when the mask body was connected to the vacuum source.

Fischer U.S. Pat. No. 4,248,218 Patented Feb. 3, 1981

That patent provided a scavenging mask apparatus for administering gas to a patient, wherein lost and exhaled gas was scavenged by vacuum means. The apparatus included a nosepiece which was adapted to fit over the patient's nose and was shaped to form a seal between the rim of the nosepiece and the patient's face. Means connected the nosepiece to a source of vacuum. A nasal cannula was disposed inside the nosepiece and attached thereto. Means were provided for connecting the cannula to a source of gas. The constant flow of gas entering the cannula was delivered directly to the patient's nostrils. Any gas escaping from the cannula, as well as gas which was exhaled through the nostrils, was scavenged by the continuous air flow inside the nosepiece and was swept toward the source of vacuum. One or more holes in the underside of the nosepiece broke the vacuum, allowing air flow for scavenging gas exhaled through the patient's mouth. The holes also prevented the mask from locking onto the patient's face due to suction.

Fischer, Jr. et al U.S. Pat. No. 4,25,239 Patented May 5, 1981

That patent provided an exhaust assembly for a gas supply system for administering gas to a patient, the system having a remote vacuum means, a scavenging mask with a peripheral chamber adjacent to the rim of the mask, means for supplying gas to the mask, means for removing exhaled gas from the mask, and an exhaust port communicating with the mask through the means for removing exhaled gas. The exhaust assembly included resistance means communicating with the exhaust port for creating a resistance to gas flow therefrom. It also included divider means for dividing gas flow, the divider means communicating with the resistance means, with the peripheral chamber, with the ambient atmosphere, and with the remote vacuum means, so that the vacuum-induced gas flow was divided between exhaled gas from the exhaust port, scavenged gas from the peripheral chamber and air from the ambient atmosphere.

Thompson, Sr. U.S. Pat. No. 4,312,339 Patented Jan. 26. 1982

That patent provided a system for administering an anaesthetic gas to a patient, including a mask, means for supplying an anaesthetic gas to the mask when the patient inhaled, and an exhaust line having its proximal end connected to the mask and adapted to have its terminal end connected to a source of vacuum to exhaust gas from the mask when the patient exhaled. A closed reservoir was in series with the exhaust line between the proximal and terminal ends thereof. The reservoir had an inlet and an outlet with a check valve adjacent to the inlet to prevent the flow of gas out of the reservoir through the inlet when the patient inhaled. A nozzle was secured to one side of the face mask for scavenging gas escaping from the mask and a second exhaust line was connected the nozzle directly to the upper end of the lower portion of the reservoir. A tube connected the upper and lower portions of the reservoir and had an opening adjacent the bottom of the lower portion of the reservoir.

Hoenig U.S. Pat. No. 4,527,558 Patented Jul. 9, 1985

That patent provided a gas scavenger system which included a collection manifold that collected the waste gases as they left the normal exhaust ports of the demand valve. A flexible tubing means then carried those collected gases to a surge chamber prior to eventual discharge into a vacuum system. The surge chamber provided an interface between the vacuum system and the collection manifold and was connected to the vacuum system through a predetermined sized orifice which limited the flow to the vacuum system to a maximum known flow. The surge chamber normally allowed continuous flow through the orifice to the vacuum system but was sized to accumulate an excess of flow from the collection manifold under abnormal conditions, such as was occasioned when a patient coughed, to allow time to remove the gases through the orifice and thus to prevent leakage to atmosphere.

Schmoegner et al U.S. Pat. No. 4,770,169 Patented Sep. 13, 1988

That patent provided an anaesthetic mask comprising a wall forming a respiratory chamber having a rim sized and configured generally to conform to a selected area surrounding the nose and/or mouth of a patient, the rim having a closed-loop perimeter and a generally "Y"-shaped cross section. An anaesthetic gas inlet was mechanically associated with the respiratory chamber for connection to an anaesthetic gas supply. An exhaust outlet was mechanically associated with the respiratory chamber for connection with a vacuum supply. A face seal was connected to the rim, the seal including, a closed-loop seal body defining a vacuum channel therein and further including a plurality of openings arranged to provide gas intercommunication between the vacuum channel and the exterior of the seal body, the seal body enclosing said rim. Vacuum connection means was included for providing gas intercommunication between the vacuum channel and the vacuum supply.

Olsson et al. U.S. Pat. No. 4,905,685 Patented Mar. 1990

That patent provided equipment for administering gaseous anaesthetic to a patient which had at least one anaesthetic reservoir serving as the originating source for anaesthetic and a ventilator to which the gas is supplied from the reservoir, the ventilator being in communication with the breathing passages of a patient. The exhalation gas from the patient was fed back to the originating anaesthetic source via at least one filter in which predetermined gas components were filtered out. The exhalation gas could then be returned to the originating source either directly or through a compressor.

Werner et al. U.S. Pat. No. 5,044,361 Patented Sep. 3, 1991

That patent provided a method and an apparatus for reuse of anesthetics in inhalation anaesthesia is described. The apparatus included a collector conduit to be connected to a patient and an anesthetics evaporator which is connected to the collector conduit via an outlet. An adsorption filter containing an adsorption material for adsorption and desorption of anaesthetic gas in gaseous form was arranged in the collector conduit distally relative to the outlet from the anesthetics evaporator, thereby leading the exhalation gas through the adsorption filter in a first direction and the inhalation gas through the adsorption filter in a second direction which was opposite to the first direction.

Burkhart U.S. Pat. No. 5,044,363 Patented Sep. 3, 1991

That patent provided an apparatus for scavenging an anaesthetic substance from a waste gas flow leaving an anaesthetic-administration system. The waste gas flow included at least a flow of unused anaesthetic in gas or vapour form and anaesthetic in the exhalation from a patient. The apparatus included means for containing a quantity of a replaceable adsorbing medium, which was disposed to receive a flow of waste gas from the anaesthetic-administration system to percolate the waste gas through the adsorbing medium for adsorption of the anaesthetic substance by the adsorbing medium. The apparatus also included means for quickly connecting and disconnecting the containing means to the anaesthetic-administration system in such a manner that the waste gas flow was caused solely by an internal pressure within the anaesthetic administration system.

Psaros et al U.S. Pat. No. 5,471,979 Patented Dec. 5, 1995

That patent provided apparatus which included means for connection to a patient via a connector for ventilating the patient with an anaesthetic gas and respiration gas, the patient thereby producing exhaled gas, in an exhalation line, containing anaesthetic gas which was not absorbed by the patient and carbon dioxide, and a remainder of exhaled gas. An adsorption filter communicated with the exhalation line for directing the exhaled gas through the adsorption filter for adsorbing the anaesthetic gas in the exhaled gas which was not adsorbed during respiration, and thereby simultaneously unavoidably adsorbing a small amount of carbon dioxide and for permitting the remainder of exhaled gas to pass through said adsorption filter means. Means were provided for evacuating the remainder of exhaled gas. An inhalation line, was provided which was separate from the exhalation line. Carbon dioxide absorber means were disposed in the inhalation line between the adsorption filter means and the connector. Means were provided for directing fresh respiration gas which had passed through the adsorption filter means through the carbon dioxide absorber for absorbing the small amount of carbon dioxide. A bypass line bypassed the adsorption filter and the carbon dioxide absorber. Means were provided for directing fresh respiration or fresh anaesthetic gas from the means for ventilating through the bypass line. Finally, means were provided for combining the gas directed through the bypass line with the fresh gas which had passed through the adsorption filter means and the carbon dioxide absorber in a desired gas concentration for forming a mixture and for supplying the mixture to the connector.

Landis et al U.S. Pat. No. 5,657,752 Patented Aug. 19, 1997

That patent provided a positive nasal airway pressure mask, including means for securing the mask to the patient's head, i.e., a head strap or harness, a primary air tube to be connected to a source of air pressure in a known manner, and a nasal mask to deliver pressurized air to the nose of the patient. The nasal mask included one or more variable orifice members with the nasal mask. The variable orifice member or members responded to increased air pressure within the mask at various stages of operation, e.g., exhalation, to relieve excess pressure.

AIMS OF THE INVENTION

A broad object of the present invention is to provide a nasal anaesthetic mask which permits scavenging of gas exhaled through the mouth when a nasal anaesthesia mask is used for the purpose of providing inhaled sedation, where such exhaled air may contain anaesthetic vapors or gases, to prevent passage of such gases to the environment.

STATEMENT OF INVENTION

The present invention provides a combined nasal anaesthesia mask and oral scavenging hood comprising a nasal anaesthesia mask, which includes an open front face which is adapted to be placed only over the nasal area of a patient to provide anaesthetic gas to the patient undergoing inhaled sedation, and rear face. An inlet is provided to an interior of the nasal anaesthesia mask by an opening in the rear face thereof, for connection to a conventional anaesthesia breathing circuit to introduce anaesthesia gas to the interior of the nasal anaesthetic mask. An oral scavenging hood is physically-associated with, or is physically associatable with respect to, the nasal anaesthetic breathing mask. The oval scavenging hood is adapted to be placed only over the mouth of the patient undergoing inhaled sedation. An inlet is provided to an interior of the oral scavenging hood for connection to the conventional scavenging circuit for scavenging exhaled gases from the area of the oral scavenging hood. The nasal anaesthesia mask interior is not in fluid communication with the scavenging hood interior. This allows continuous, uninterrupted flow of anaesthesia gas to the patient while substantially simultaneously scavenging exhaled gases from the interior of the oral scavenging hood.

OTHER FEATURES OF THE INVENTION

One feature of this invention the oral scavenging hood is physically connected to the nasal anaesthesia breathing mask. By three specific features of that feature, the separate scavenging hood is connected to the nasal anaesthesia mask by a direct connection to a ring connector element at the rear of the nasal anaesthesia mask; or is physically connected to the nasal anaesthesia mask by being slipped over the rear face of the nasal anaesthesia mask and by being held thereto by friction; or is pivotally secured to the nasal anaesthesia mask, whereby the oral scavenging hood can be swung downwardly to enshroud the mouth of a patient undergoing inhaled sedation, and can be swung upwardly for interrupting the enshrouding.

By still another feature of this invention the nasal anaesthesia mask and the oral scavenging hood are combined as an integral monolithic unit. By a specific feature of that feature, the oral scavenging hood is formed integrally with a base of the nasal anaesthesia mask. By another feature of that feature, the oral scavenging hood is secured to the base of the nasal anaesthesia mask. By still another feature of this feature of this invention, the oral scavenging hood is detachedly secured to the base of the nasal anaesthesia hood.

By still a further feature of this invention, the scavenging hood includes a connector for attachment to a conventional scavenging system.

Includes a "Y" connector which is incorporated into the conventional nasal anaesthesia scavenging system, thereby to enable connection both to the conventional nasal anaesthesia mask and to the oral scavenging hood.

By a still further feature of this invention, the oral scavenging hood adapted to be adjacent to the mouth of the patient, so that it is not in contact with the face of the patient.

By yet a still further feature of this invention, the oral scavenging hood is adapted to be in removable contact with the face of the patient and which forms an air-tight seal around the mouth of the patient.

DESCRIPTION OF FIGS. 1 TO 4

Figure 1:
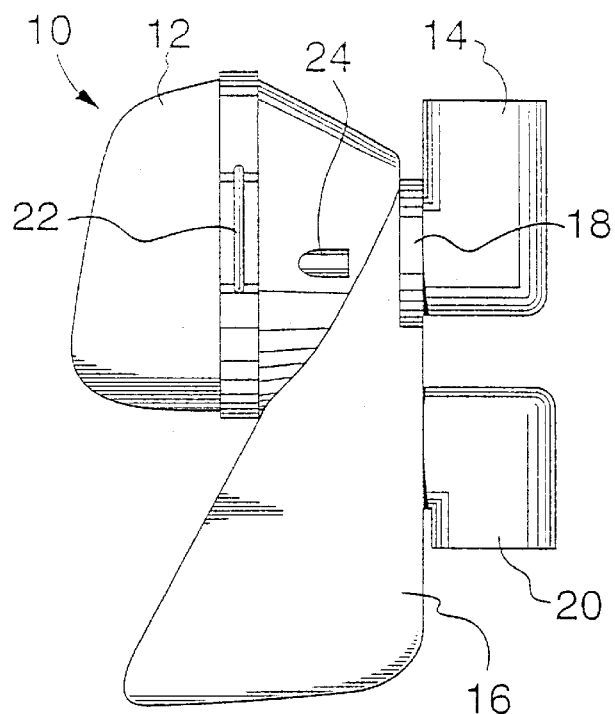
FIG. 1 is a side elevational view of a first embodiment of a combined nasal anaesthesia breathing mask and oral scavenging hood of the present invention, wherein the oral scavenging hood is a separate element for connection to the nasal anaesthesia mask for placement only over the mouth of the patient undergoing inhaled sedation, wherein the oral scavenging hood is in its attached mode.

As seen in FIGS. 1 to 4, inclusive, a first embodiment of this invention 10 includes a conventional nasal anaesthesia breathing mask 12 which includes a connector 14, e.g., a 22-mm OD, "L"-shaped connector for connection to a conventional anaesthesia breathing circuit (not seen). An oral scavenging hood 16 is directly connected to the conventional nasal anaesthesia breathing mask 12 by means of a ring connector element 18 at the rear of the nasal anaesthesia breathing mask 12, the ring connector 18 having, e.g., a 22-mm ID. The oral scavenging hood 16 is connected by means of a connector 20, e.g., an "L"-shaped connector having, e.g., a 19-mm ID to a conventional scavenging circuit (not seen). As is conventional, the nasal anaesthesia breathing mask 12 is provided with a sampling port 24.

Figure 2:
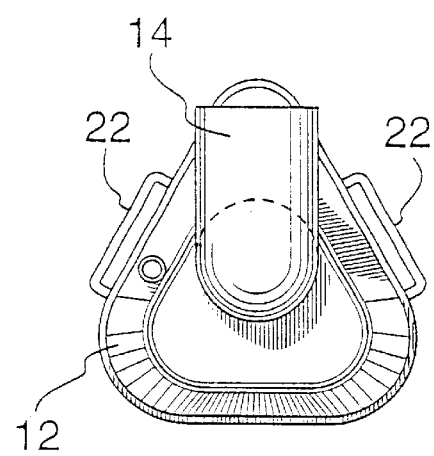
FIG. 2 is a front elevational view of the nasal anaesthesia breathing mask only forming part of the combined nasal anaesthesia breathing mask and oral scavenging hood of the first embodiment of the invention shown in FIG. 1.
Figures 3, 4:
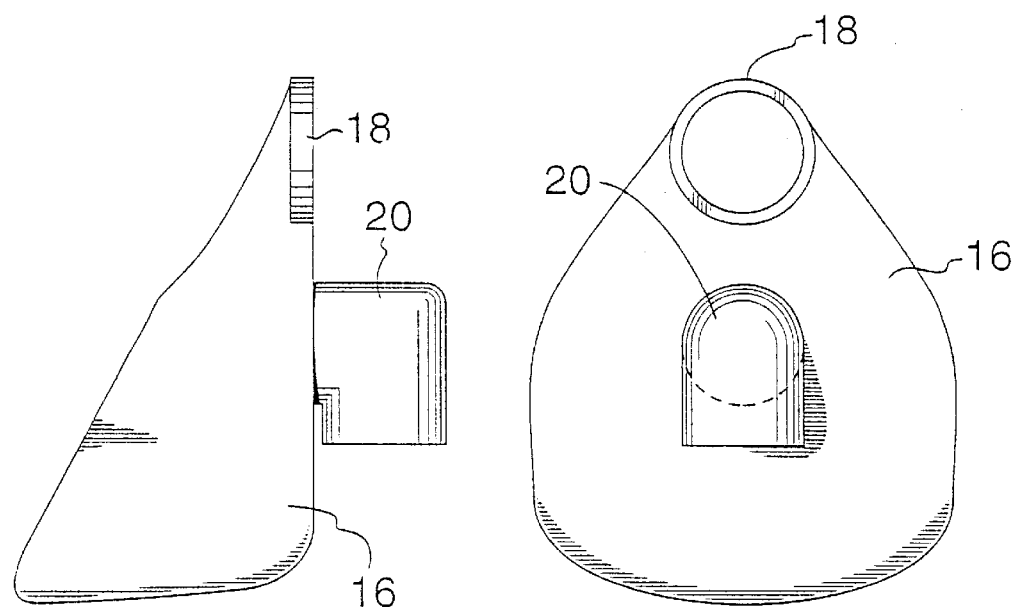
FIG. 3 is a side elevational view of the oral scavenging hood only forming part of the combined nasal anaesthesia breathing mask and oral scavenging hood of the first embodiment of the invention shown in FIG. 1.
FIG. 4 is a front elevational view of the oral scavenging hood only forming part of the combined nasal anaesthesia breathing mask and scavenging hood of the first embodiment of the invention as shown in FIG. 1.

As more clearly seen in FIG. 2, the nasal anaesthesia breathing mask 12 is adapted to be secured to a patient undergoing inhaled sedation in the conventional manner, i.e., by means of straps (not seen) which are connected to strap loops 22 which are integral with, or which form part of, the conventional nasal anaesthesia breathing mask 12.

DESCRIPTION OF FIGS. 5 AND 6

Figure 5:
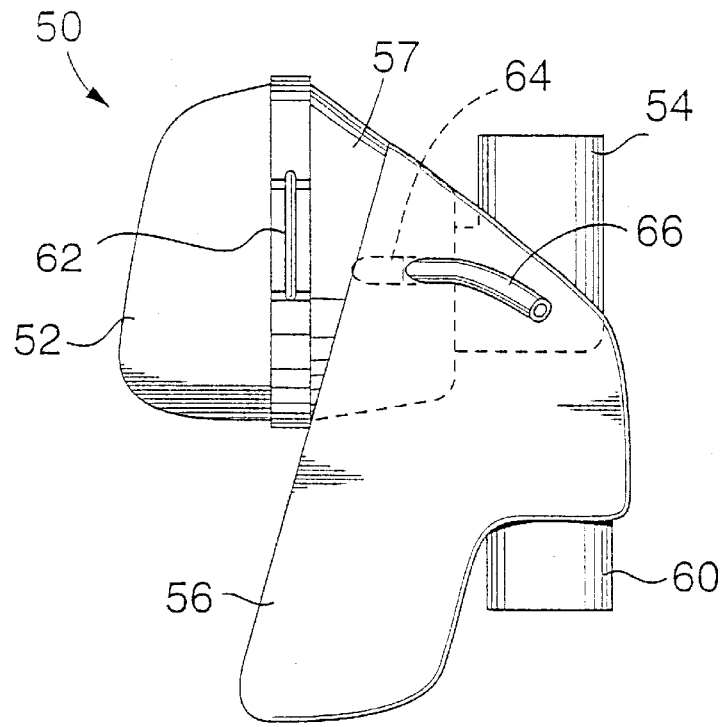
FIG. 5 is a side elevational view of a second embodiment of a combined nasal anaesthesia breathing mask and oral scavenging hood of the present invention, wherein the oral scavenging hood is a separate element but is secured to the nasal anaesthesia breathing mask by friction for placement only over the mouth of the patient undergoing inhaled sedation.
Figure 6:
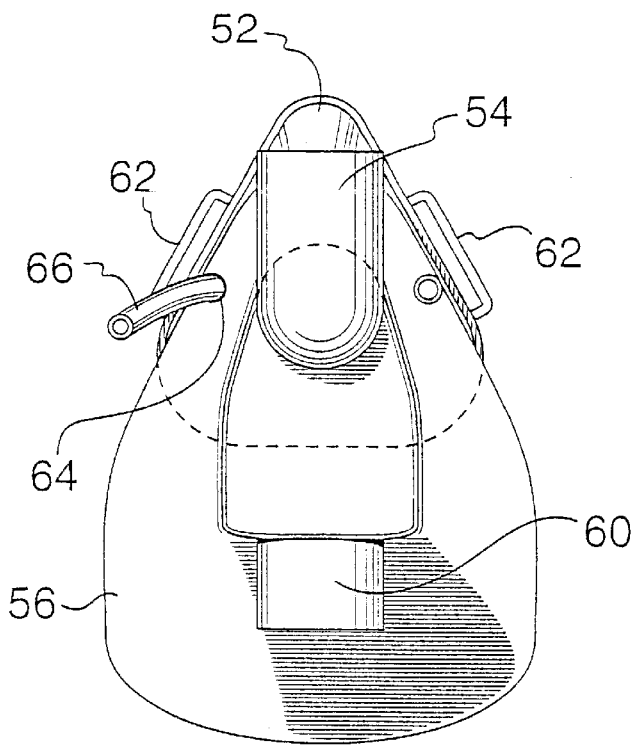
FIG. 6 is a front elevational view of the combination of the nasal anaesthesia breathing mask and the oral scavenging hood of the second embodiment of the invention shown in FIG. 5.

As seen in FIGS. 5 and 6, a second embodiment of this invention 50 includes a conventional nasal anaesthesia breathing mask 52 which has been modified by including a second version of a selectively attachable and detachable oral scavenging hood 56 which slips over the rear faces 57 of the conventional nasal anaesthesia breathing mask 52, and is held thereon by friction. The conventional nasal anaesthetic breathing mask 52 also includes a connector 54, e.g., a 22 mm OD, "L"-shaped connector for connection to a conventional anaesthetic breathing circuit (not seen). The oral scavenging hood 56 is connected by a connector 60, e.g., having a 19 mm OD, to a conventional scavenging circuit (not seen). It is thus not necessary to disconnect the attachment of the nasal anaesthesia breathing mask from the conventional anaesthesia breathing circuit, and to reconnect the oral scavenging hood and the anaesthesia mask again by means of a ring connector element at the rear of the nasal anaesthesia mask, as was described for the first embodiment of this invention.

The conventional sampling port 64 of the nasal anaesthetic breathing mask 52 is connected to a sampling tube 66 on the oral scavenging hood 56. The nasal anaesthetic breathing mask 52 is also provided with strap hooks 62 to enable securement of the nasal anaesthetic breathing mask 52 to a patient by means of a strap (not seen).

DESCRIPTION OF FIGS. 7 AND 8

Figure 7:
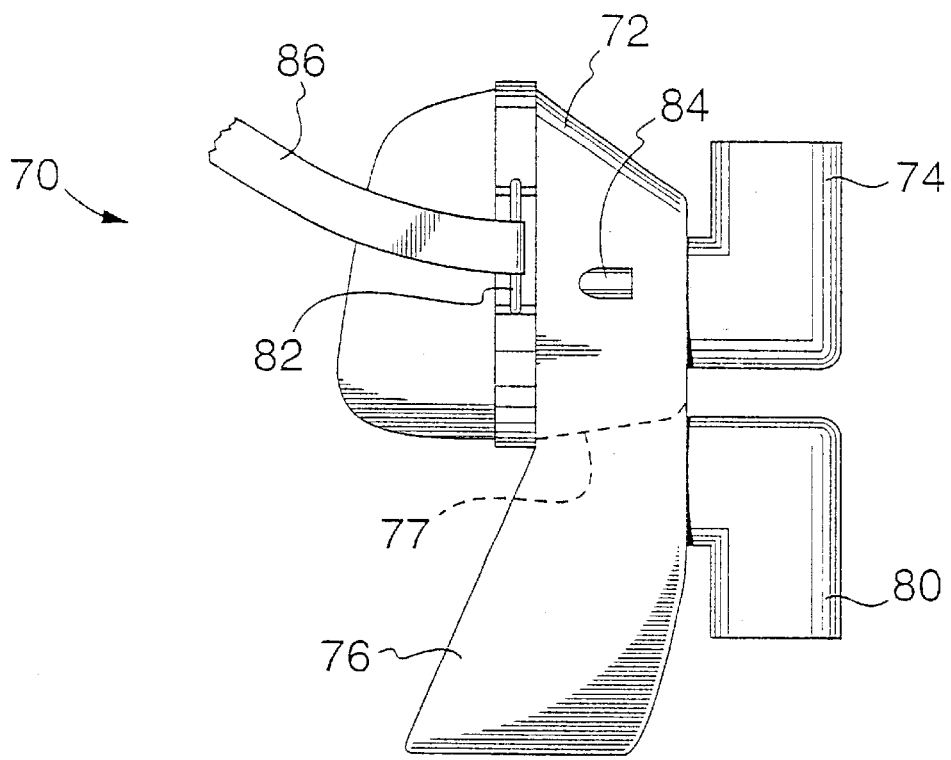
FIG. 7 is a side elevational view of a third embodiment of a combined nasal anaesthesia breathing mask and oral scavenging hood of the present invention, wherein the oral scavenging hood is integral with the nasal anaesthesia mask for placement only over the mouth of the patient undergoing inhaled sedation.
Figure 8:
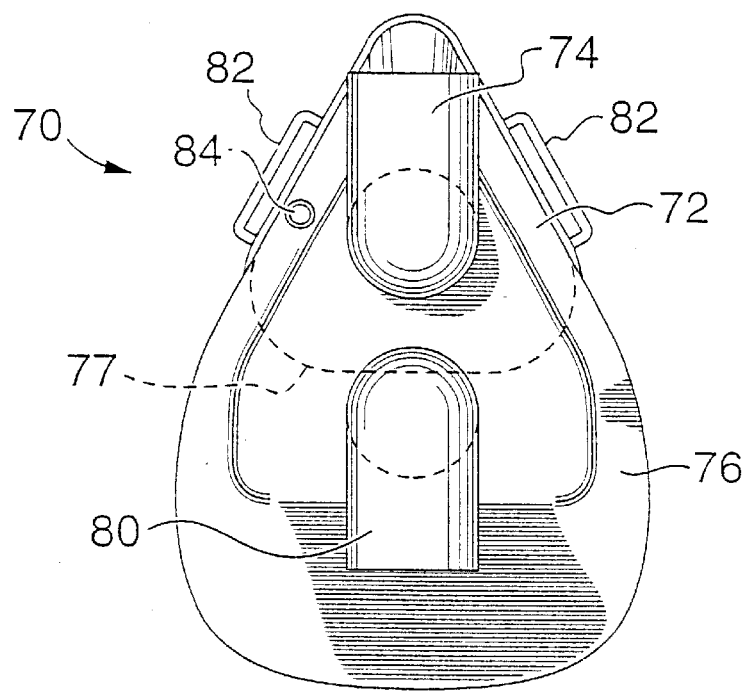
FIG. 8 is a front elevational view of the combination of the nasal anaesthesia breathing mask and the oral scavenging hood of the third embodiment of the invention shown in FIG. 7.
Figure 9:
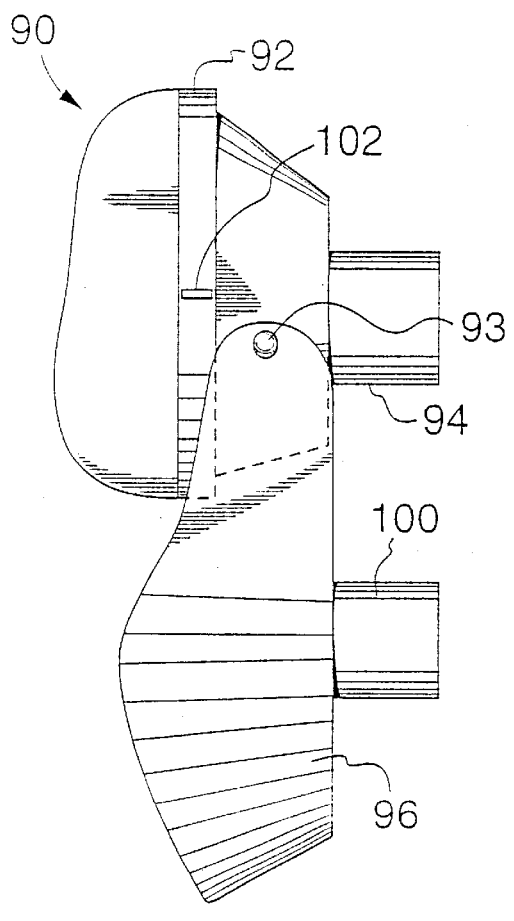
FIG. 9 is a side elevational view of a fourth embodiment of a combined nasal anaesthesia breathing mask and oral scavenging hood, wherein the oral scavenging hood is a separate element which is pivotally connected to the nasal anaesthesia breathing mask for placement over only the mouth of the patient undergoing inhaled sedation, wherein the oral scavenging hood is in its operative mode.
Figure 10:
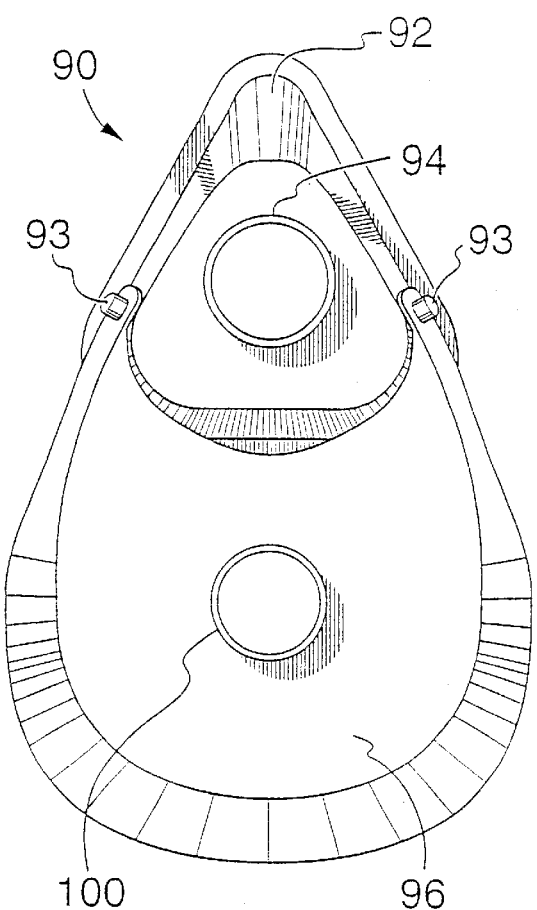
FIG. 10 is a front elevational view of the combined nasal anaesthesia breathing mask and oral scavenging hood of the fourth embodiment of the invention shown in FIG. 9.
Figure 11:
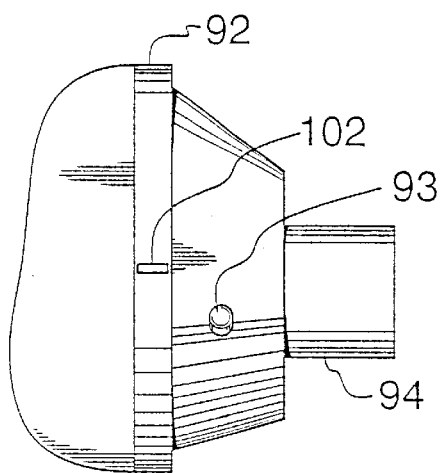
FIG. 11 is a side elevational view of the nasal anaesthesia breathing mask only forming part of the combined nasal anaesthesia breathing mask and oral scavaging hood of the fourth embodiment of the invention shown in FIG. 9.
Figure 12:
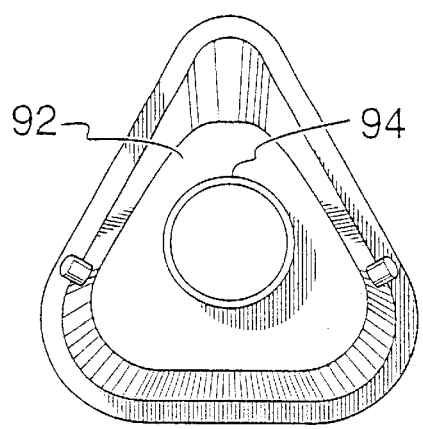
FIG. 12 is a front elevational view of the nasal anaesthesia breathing mask only forming part of the combined nasal anaesthesia breathing mask and oral scavaging hood of the fourth embodiment of the invention, shown in FIG. 9.
Figure 13:
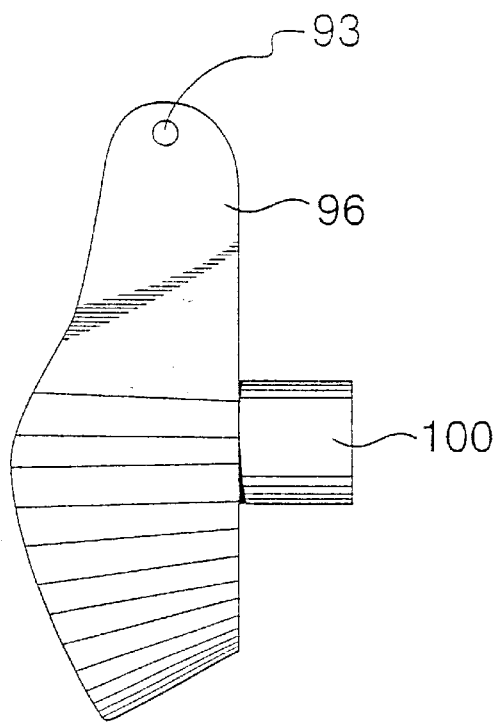
FIG. 13 is a side elevational view of the oral scavenging hood only forming part of the combined nasal anaesthesia breathing mask and oral scavaging hood of the fourth embodiment of the invention shown in FIG. 9.
Figure 14:
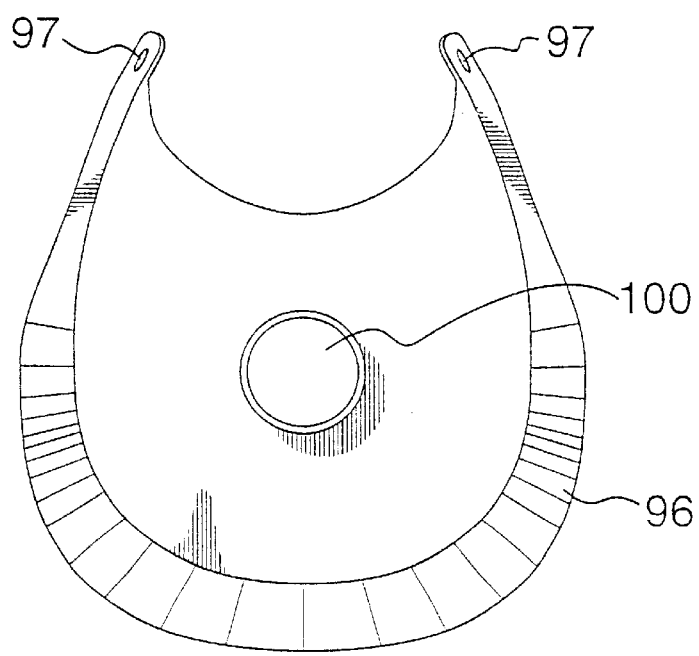
FIG. 14 is a front elevational view of the nasal anaesthesia mask only forming part of the combined nasal anaesthesia breathing mask and oral scavaging hood of the fourth embodiment of the invention shown in FIG. 9.

As seen in FIGS. 7 and 8, a third embodiment of this invention 70 includes a conventional nasal anaesthesia breathing mask 72 which has been modified by including an integral oral scavenging hood 76 which is either formed integral with, or is integrally attached to the base thereof 77.

The heretofore conventional nasal anaesthetic breathing mask 72 includes a connector 74, e.g., a 22 mm OD, "L"-shaped connector for connection to a conventional anaesthetic breathing circuit (not seen). The oral scavenging hood 76 is part of the nasal anaesthetic breathing mask 72 by means of connection to the base 77 thereof. The oral scavenging hood 76 is connected by a connector "L"-shaped 80, e.g., having a 19 mm OD, to a conventional scavenging circuit (not seen).

The nasal anaesthetic breathing mask 72 is also provided with a sampling port 84. The nasal anaesthetic breathing mask 72 is also provided with strap hooks 82 to enable securement of the nasal anaesthetic breathing mask 72 to a patient by means of strap 86.

DESCRIPTION OF FIGS. 9 TO 14

As seen in FIGS. 9 to 14, a fourth embodiment of this invention 90 includes a heretofore conventional nasal anaesthesia breathing mask 92 which has been modified by including a fourth version of a selectively attachable and detachable oral scavenging hood 96 thereon, e.g., by being pivoted to the nasal anaesthesia breathing mask 92 at pivot pin 93. The heretofore conventional anaesthetic breathing mask 92 also includes a connector 94, e.g., a 22 mm OD, "L"-shaped connector, for connection to a conventional anaesthetic breathing circuit (not seen). This oral scavenging hood 96 is connected to the conventional nasal anaesthetic breathing mask 92 by engaging the bores 97 therethrough within pivot pins 93 which are provided on the nasal anaesthetic breathing mask 92. The oral scavenging hood 96 is connected by a connector 100 e.g., having a 19 mm OD to a conventional scavenging circuit (not seen).

The nasal anaesthesia breathing mask 92 is adapted to be secured to a patient undergoing inhaled sedation in the conventional manner, i.e., by means of straps (not seen) which are connected to strap loops 102 which are integral with, or which form part of, the nasal anaesthesia breathing mask 92.

GENERALIZED DESCRIPTION

By the use of various embodiments of the present invention, contamination of operating room air with anaesthetic vapors or gases is prevented or reduced. In addition, the oral scavenging hood is easily and quickly removed if it is necessary, or if the patient needs to vomit, talk, or feels confined, etc. This can be done, according to embodiments of the present invention, without removing the nasal anaesthesia mask, which would increase the contamination or result in reduced patient sedation.

From the above description and drawings, it is seen that the present invention, in its various embodiments, includes the following variations:

Where a separate conventional nasal anaesthesia mask is used, a separate oral scavenging hood is used which either fits over the anaesthesia breathing system connector, or which attaches to the conventional nasal anaesthesia mask by other means, e.g., by means of an O-ring, or by a pivotal connection.

Where a single device is used, a nasal anaesthesia mask is incorporated along with an attached or detachable oral scavenging hood.

Where the oral scavenging hood is not in contact with the face of the patient but is disposed so that it is only adjacent to the mouth of the patient.

Where the oral scavenging hood is in contact with the face of the patient and forms an air-tight seal around the mouth of the patient, but which nevertheless is removable.

Where the oral scavenging hood incorporates a standard 19-mm connector for attachment to the conventional nasal anaesthesia scavenging system.

Where a standard 19-mm "Y" connector is incorporated into the conventional nasal anaesthesia scavenging system to enable connection both to the conventional nasal anaesthesia breathing mask and to the oral scavenging hood.

CONCLUSION

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

What is claimed is:

1. A combined nasal anaesthesia mask and oral scavenging hood, comprising:

(a) a nasal anaesthesia breathing mask, said nasal anaesthesia breathing mask including an open front face adapted to be placed only over the nasal area of a patient of a patient to provide anaesthesia gas to the patient undergoing inhaled sedation, and a rear face;

(b) an inlet to an interior of said nasal anaesthesia mask via an opening in said rear face thereof for connection to a conventional anaesthesia breathing circuit to introduce anaesthesia gas to the interior of said nasal anaesthesia mask;

(c) an oral scavenging hood which is physically connected to said nasal anaesthesia breathing mask and which is adapted to be placed only over the mouth of the patient undergoing inhaled sedation; and (d) an inlet means to an interior of said oral scavenging hood for connection to a convention scavenging circuit, for scavenging exhaled gases from the interior of said oral scavenging hood;

said nasal anesthesia mask interior not being in fluid communication with said scavenging hood interior;

thereby allowing continuous, uninterrupted flow of anaesthesia gas to said patient while substantially-simultaneously scavenging exhaled gases from the interior of said oral scavenging hood.

2. The combined nasal anaesthesia mask and oral scavenging hood of claim 1, wherein said oral scavenging hood is physically-connected to said nasal anaesthesia breathing mask by a direct connection to a ring connector element at the rear face of said nasal anaesthesia mask.

3. The combined nasal anaesthesia breathing mask and oral scavenging hood of claim 1, wherein said oral scavenging hood is a physically-connected to said nasal anaesthesia mask by being slipped over the rear face of said nasal anaesthesia breathing mask and by being held thereto by friction.

4. The combined nasal anaesthesia breathing mask and oral scavenging hood of claim 1, wherein said oral scavenging hood is physically-connected to said nasal anaesthesia breathing mask, whereby said oral scavenging hood is configured to be swung downwardly to enshroud the mouth of a patient undergoing inhaled sedation, and is configured to be swung upwardly for interrupting said enshrouding.

5. The combined nasal anaesthesia breathing mask and oral scavenging hood of claim 1, wherein said nasal anaesthesia breathing mask and said oral scavenging hood are combined as an integral, monolithic unit.

6. The combined nasal anaesthesia breathing mask and oral scavenging hood of claim 5, wherein said oral scavenging hood is formed integrally with a base of said nasal anaesthesia mask.

7. The combined nasal anaesthesia mask and oral scavenging hood of claim 6, wherein said oral scavenging hood is secured to a base of said nasal anaesthesia mask.

8. The combined nasal anaesthesia mask and oral scavenging hood of claim 7 wherein said oral scavenging hood is detachably-secured to said base of said nasal anaesthesia mask.

9. The combined nasal anaesthesia breathing mask and oral scavenging hood of claim 1, wherein said oral scavenging hood includes a standard connector for attachment to a conventional scavenging system.

10. The combined nasal anaesthesia mask and oral scavenging hood of claim 1, wherein said oral scavenging hood is adapted to be adjacent only to the mouth of the patient, and so that it is not in contact with the face of the patient.

11. The combined nasal anaesthesia mask and oral scavenging hood of claim 1, wherein said oral scavenging hood is adapted to be in removable contact with the face of the patient and forms an air-tight seal around the mouth of said patient.

* * * * *